(12) United States Patent
Lam

(10) Patent No.: US 9,504,407 B2
(45) Date of Patent: Nov. 29, 2016

(54) METHOD AND SYSTEM FOR PROCESSING RUNNER DATA

(71) Applicant: Chin Keong Lam, Palo Alto, CA (US)

(72) Inventor: Chin Keong Lam, Palo Alto, CA (US)

(*) Notice: Subject to any disclaimer, the term of this patent is extended or adjusted under 35 U.S.C. 154(b) by 199 days.

(21) Appl. No.: 14/284,016

(22) Filed: May 21, 2014

(65) Prior Publication Data

US 2014/0350435 A1   Nov. 27, 2014

Related U.S. Application Data

(60) Provisional application No. 61/855,657, filed on May 21, 2013.

(51) Int. Cl.
*A61B 5/05* (2006.01)
*A61B 5/11* (2006.01)
*A61B 5/00* (2006.01)
*A61B 5/103* (2006.01)

(52) U.S. Cl.
CPC ............. *A61B 5/112* (2013.01); *A61B 5/1038* (2013.01); *A61B 5/1121* (2013.01); *A61B 5/6807* (2013.01); *A61B 2560/0425* (2013.01); *A61B 2562/0247* (2013.01); *A61B 2562/164* (2013.01); *A61B 2562/168* (2013.01)

(58) Field of Classification Search
CPC .. A61B 5/112; A61B 5/1121; A61B 5/6807; A61B 5/1038; A61B 2562/164; A61B 2562/168
See application file for complete search history.

(56) References Cited

U.S. PATENT DOCUMENTS

| | | | | |
|---|---|---|---|---|
| 5,107,854 A * | 4/1992 | Knotts | ............... | A61B 5/1036 340/626 |
| 6,301,964 B1 * | 10/2001 | Fyfe | ................... | A63B 69/0028 702/160 |
| 7,426,873 B1 * | 9/2008 | Kholwadwala | ......... | A43B 3/00 73/777 |
| 2003/0163287 A1 * | 8/2003 | Vock | .................... | A43B 3/0005 702/187 |
| 2005/0166373 A1 * | 8/2005 | Saaski | ...................... | A61B 5/11 24/712.1 |
| 2005/0172463 A1 * | 8/2005 | Rolla | ...................... | A43C 7/02 24/712.1 |
| 2009/0069865 A1 * | 3/2009 | Lasko | .................. | A61B 5/1038 607/49 |
| 2009/0192759 A1 * | 7/2009 | Wedge | ................ | A43B 3/0005 702/160 |
| 2010/0152619 A1 * | 6/2010 | Kalpaxis | .............. | A61B 5/0002 600/592 |
| 2010/0198111 A1 * | 8/2010 | Milani | ................. | A43B 3/0005 600/592 |
| 2010/0211355 A1 * | 8/2010 | Horst | ................... | A61B 5/1038 702/173 |
| 2011/0054359 A1 * | 3/2011 | Sazonov | .............. | A43B 3/0005 600/595 |
| 2011/0087445 A1 * | 4/2011 | Sobolewski | ......... | A43B 1/0054 702/44 |
| 2012/0291564 A1 * | 11/2012 | Amos | .................. | G01C 22/006 73/862.045 |
| 2013/0041617 A1 * | 2/2013 | Pease | .................. | A43B 3/0005 702/139 |
| 2013/0061497 A1 * | 3/2013 | Antonovich | ............. | A43C 9/02 36/136 |
| 2013/0192071 A1 * | 8/2013 | Esposito | ............. | A61B 5/1036 33/6 |
| 2013/0213147 A1 * | 8/2013 | Rice | .......................... | G01L 1/20 73/862.046 |

* cited by examiner

Primary Examiner — Michael C Stout

(57) ABSTRACT

In an embodiment, a system for processing runner data includes a pressure sensor set having a first pressure sensor disposed in a footbed, the first pressure sensor including a first polyolefin sheet and a first gas chamber formed at least in part by the first polyolefin sheet, an electronics module coupled to the pressure sensor set, the electronics module including a first accelerometer, and a second accelerometer.

19 Claims, 16 Drawing Sheets

METHOD AND SYSTEM FOR PROCESSING RUNNER DATA

CROSS REFERENCE TO RELATED APPLICATION

This application claims the benefit of U.S. provisional application Ser. No. 61/855,657, filed on May 21, 2013, the entirety of which is incorporated herein by reference.

BACKGROUND

Technical Field

This invention relates to runner data, and more particularly to a method and system for processing runner data.

Description of the Related Art

Running can provide multiple health benefits, including improving fitness, reducing the chance of heart disease, and improving overall well being. Among the challenges faced by runners, injury is one potential risk that can prevent beginning runners from achieving significant progress. One source of injury is how runners place their feet while running, including how the runner's foot impacts the ground between fore foot and rear foot and whether the foot rolls to one side or the other.

Although information may help prevent such injuries, conventional systems may be too difficult, costly, or inconvenient for most runners. For example, in some conventional systems, runner data is collected through treadmills with built-in force measurement systems. Such conventional systems may be costly, immobile, and inefficient.

In other conventional systems, costly, inefficient, or ineffective sensors may be used to collect data, which may also be collected incompletely. Such systems may be avoided by potential customers due to one or more of the inconveniences.

Accordingly, improvements may be made over conventional methods and systems.

SUMMARY

In an aspect, a system for processing runner data includes a pressure sensor set having a first pressure sensor disposed in a footbed, the first pressure sensor including a first polyolefin sheet and a first gas chamber formed at least in part by the first polyolefin sheet (e.g., a conductive polyolefin sheet), an electronics module coupled to the pressure sensor set, the electronics module including a first accelerometer, and a second accelerometer.

The first pressure sensor may include a second polyolefin sheet, the gas chamber being formed in part by the second polyolefin sheet. The first polyolefin sheet and the second polyolefin sheet may be bonded together at a perimeter that encircles the first gas chamber. The first gas chamber may enlarge a pressure sensing range of the first pressure sensor.

The electronics module may be coupled to the first pressure sensor via a first conductor and a ground conductor. The pressure sensor set may include a second pressure sensor comprising a third polyolefin sheet and a second gas chamber formed at least in part by the third polyolefin sheet. The electronics module may be coupled to the first pressure sensor using a first conductor and a third conductor, and the electronics module may be coupled to the second pressure sensor using a second conductor and the third conductor.

The electronics module may include a third accelerometer. The electronics module may include a housing formed with two slots that are oppositely disposed on the housing, each slot being configured to receive at least one shoelace that secures the electronics module to a shoe. Each slot may include a flexible flange that extends across the slot opening, the flange being configured to bend when a shoelace is pressed into the slot, and to spring back into place after the shoelace has been pressed far enough into the slot to pass the flange.

The footbed may be a removable shoe sole, part of a shoe sole, a cushion inside a shoe, and/or bonded to a shoe.

The system may automatically recalibrates its sensitivity when the accelerometers detect that a user is not moving and that the output of the pressure sensor has held a maximum output level for more than a threshold period of time.

The system may be configured to wirelessly relay accelerometer data and pressure sensor data to a smartphone for developing a runner profile. The runner profile may indicate whether at least one of the user's feet rotates improperly around a roll axis (e.g., an axis extending between a user's toes and heel).

In another aspect, a system for processing runner data includes a pressure sensor set having a first pressure sensor and a second pressure sensor each disposed in a removable shoe insert, each of the first pressure sensor and the second pressure sensor including a first polyolefin sheet, a second polyolefin sheet, and a gas chamber formed at least in part by the first polyolefin sheet and the second polyolefin sheet. The system further includes an electronics module coupled to the pressure sensor set, the electronics module including a first accelerometer, a second accelerometer, and a third accelerometer, the electronics module having a housing configured to be secured to the top of a user's running shoe.

The first polyolefin sheet and the second polyolefin sheet may be bonded (e.g., glued, clamped, fused together, etc.) together at a perimeter that encircles each enclosed gas chamber. Each gas chamber may enlarge a pressure sensing range of the first pressure sensor and the second pressure sensor. The electronics module may be coupled to the first pressure sensor via a first conductor and a ground conductor, and the electronics module may be coupled to the second pressure sensor via the second conductor and the ground conductor.

DESCRIPTION OF EXEMPLARY EMBODIMENTS

Exemplary embodiments of the invention are described in detail below. Note that the following exemplary embodiments do not in any way limit the scope of the invention. Note also that all of the elements described in connection with the following exemplary embodiments should not necessarily be taken as essential elements of the invention.

I. Overview

In some embodiments, the system may utilize a new sensor system for detecting runner footfalls. This pressure sensor data may be combined with accelerometer data that is collected from a module that is attached to at least one of the runner's shoes.

The pressure sensor unit may include multiple sensors that permit detection of pressure at a user's forefront and at the user's heel, which may help the user determine whether their running style is safe, efficient, or needs improvement.

The pressure sensors used in the pressure sensor unit may be formed from one or more polyolefin sheets (e.g., conductive polyolefin sheets) that form a flexible air chamber. In other embodiments, different gasses such as Nitrogen may be used. By changing in resistance while the flexible air chamber is compressed and/or deformed, the sensor unit may have a substantially increased pressure sensitivity range over conventional polyolefin sheets.

When the data from the pressure sensor unit is combined with accelerometer data from the accelerometer unit, the system may provide more accurate information with respect to whether a user is hitting the ground primarily with their forefoot, their heel, or if they have a balanced running style. The system may further be able to determine whether the runner runs with proper form with respect to over or under pronation (e.g., a rolling lateral movement of the foot at the ankle).

The system may collect data from one or more accelerometers to create a profile of the user's running form, and may continuously update an app running on the user's smartphone. This data may in turn be shared online via a social network where users can compare data, provide comments and feedback, and/or provide encouragement.

II. System Operation

A. Force Measurement

Figure 1:
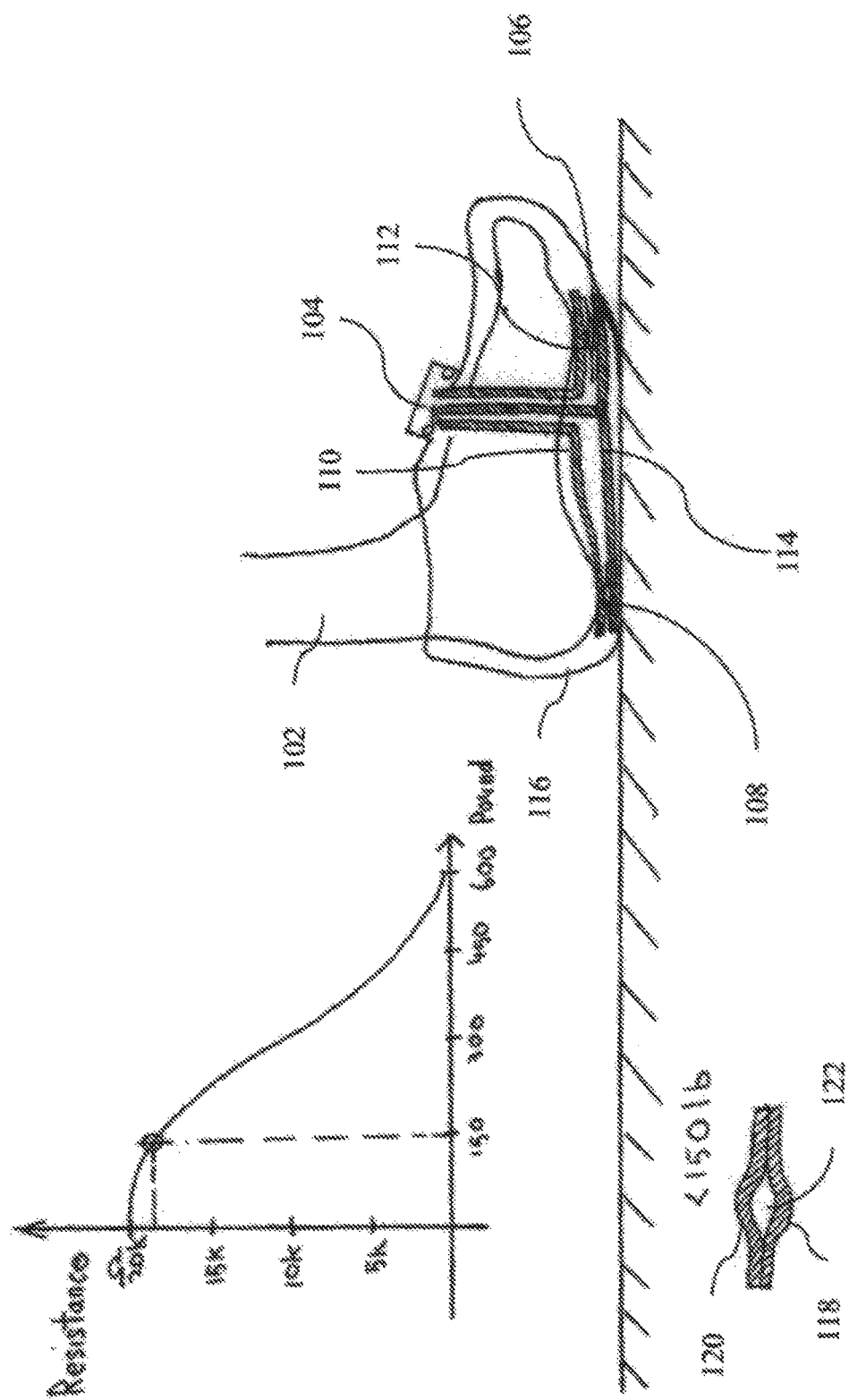
FIGS. 1, 2, and 3 are illustrations of operation of components of the system, according to an embodiment.
Figure 2:
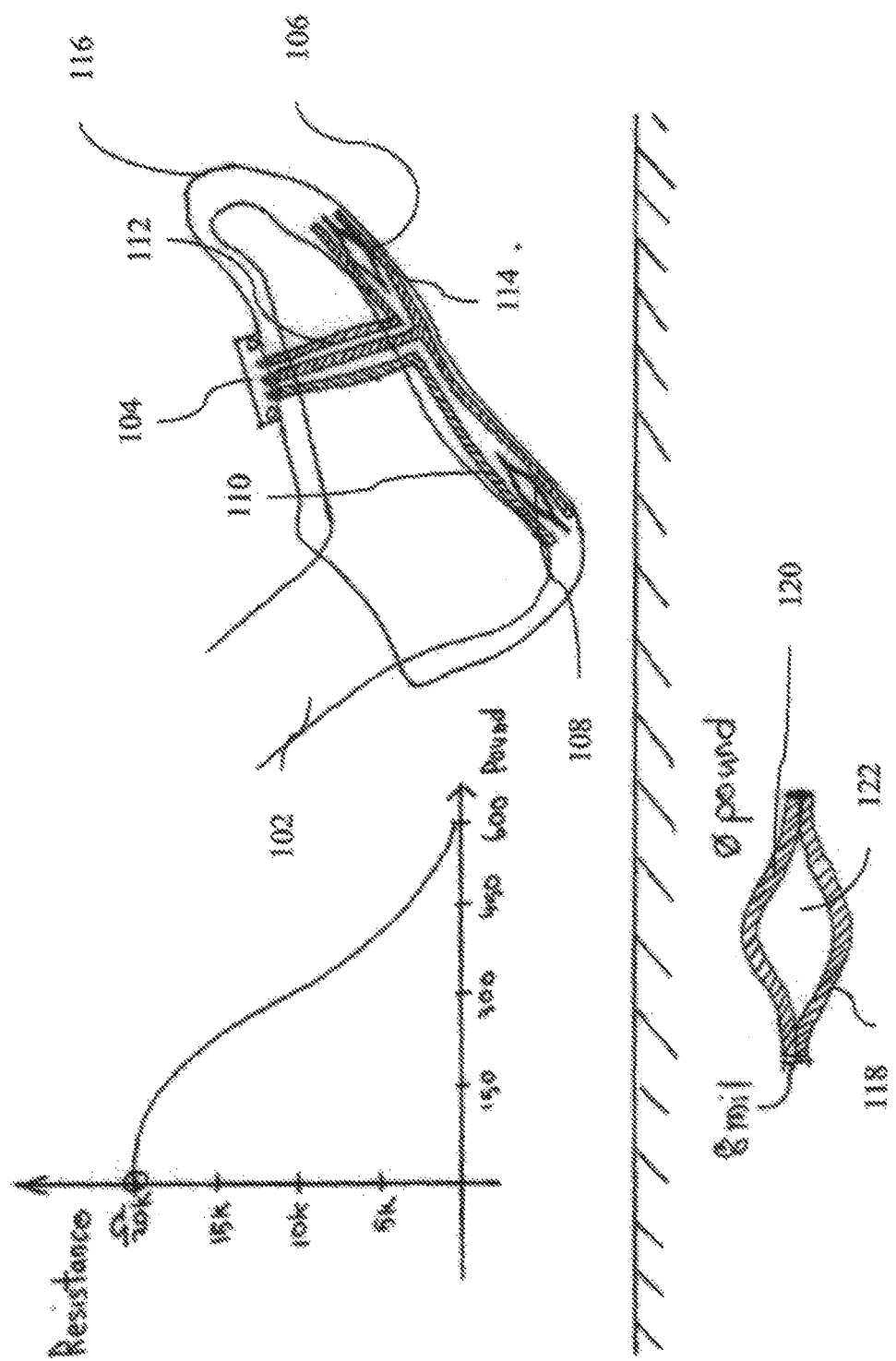
Figure 3:
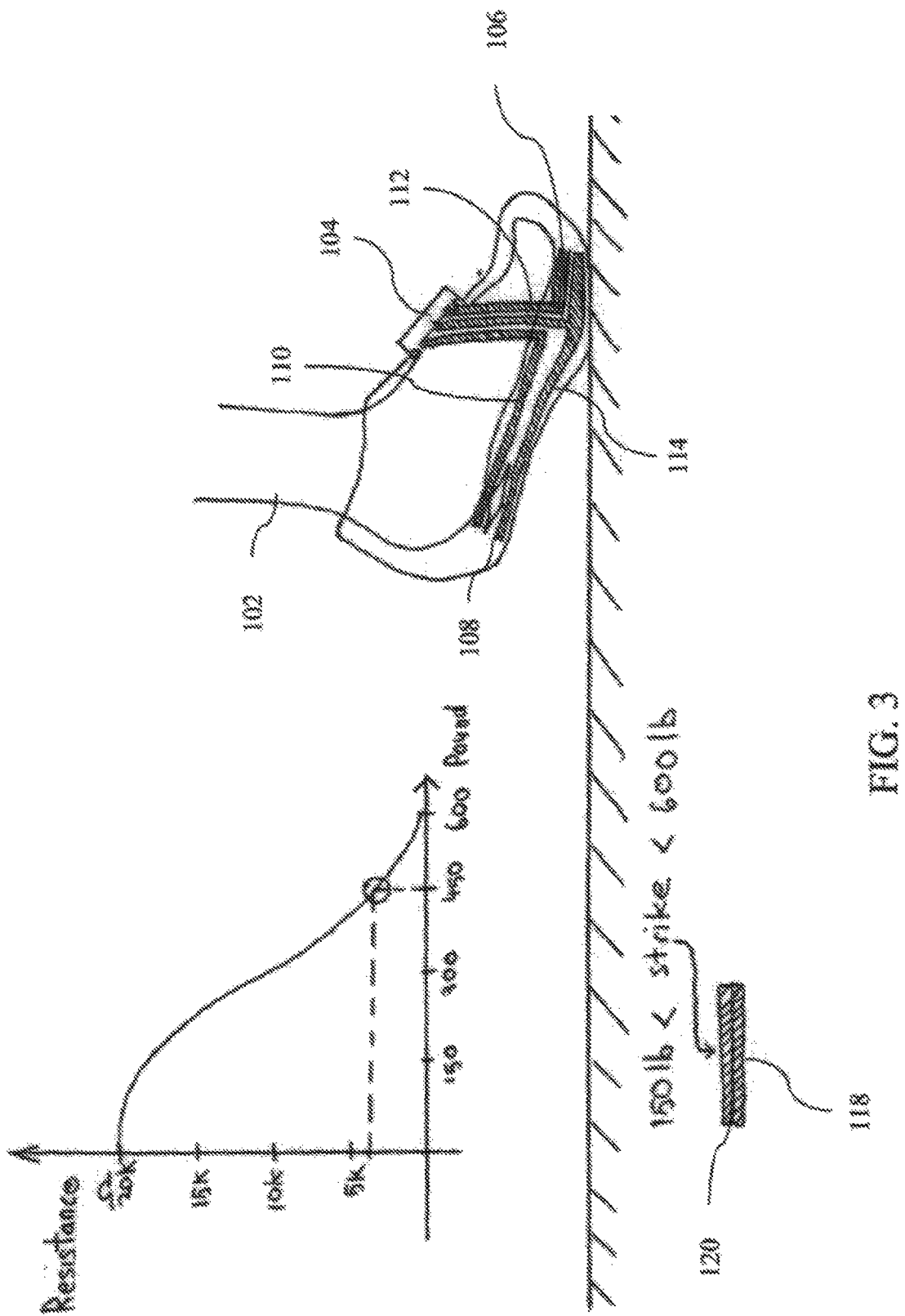

FIGS. 1 to 3 include a runner's leg 102, a shoe 116, an electronics module 104, a front sensor 106, a rear sensor 108, a first conductor 110, a second conductor 112, and a third conductor 114.

Each of the front sensor 106 and the rear sensor 108 may include the bottom polyolefin layer 118 and the top polyolefin layer 120, in between which may be an air chamber 122 formed by a bonding between the bottom layer 118 and the top layer 120 around a lateral circumference of the air gap 122.

The electronics module may include one or more accelerometers (e.g. linear accelerometers, biaxial, or triaxial linear and/or rotational accelerometers) and a bluetooth transceiver for communicating with a user's mobile device.

As shown in FIG. 1, when the runner is simply standing, the air chamber 122 may be partially compressed at an intermediate air pressure level, which may correspond to an intermediate resistance level (e.g., 18 Ohms) and an intermediate pressure value (e.g., 150 pounds).

As shown in FIGS. 2 and 3, while the runner is running, varying conditions may occur. As shown in FIG. 2, when the runner's foot is lifted off the ground, the calibrated air pressure of the air chamber may be at a lower pressure level. The resistance of each of the sensors may be at their greatest, at 20 kΩ, which may correspond to a zero weight amount.

As shown in FIG. 3, when the user's weight has been applied to the forward sensor by the forefront of the user's foot, the forward sensor may be compressed such that the air gap 122 has been reduced substantially, and the upper polyolefin layer 120 and the lower polyolefin layer 118 are moved into substantially greater contact. At this stage, the pounds of force detected by the front sensor 106 may be an upper force measurement (e.g., approximately 450 lbs.), and the resistance may be at a lower level (e.g., less than 5 kΩ).

B. Exemplary Pressure Sensor Components

Figure 4:
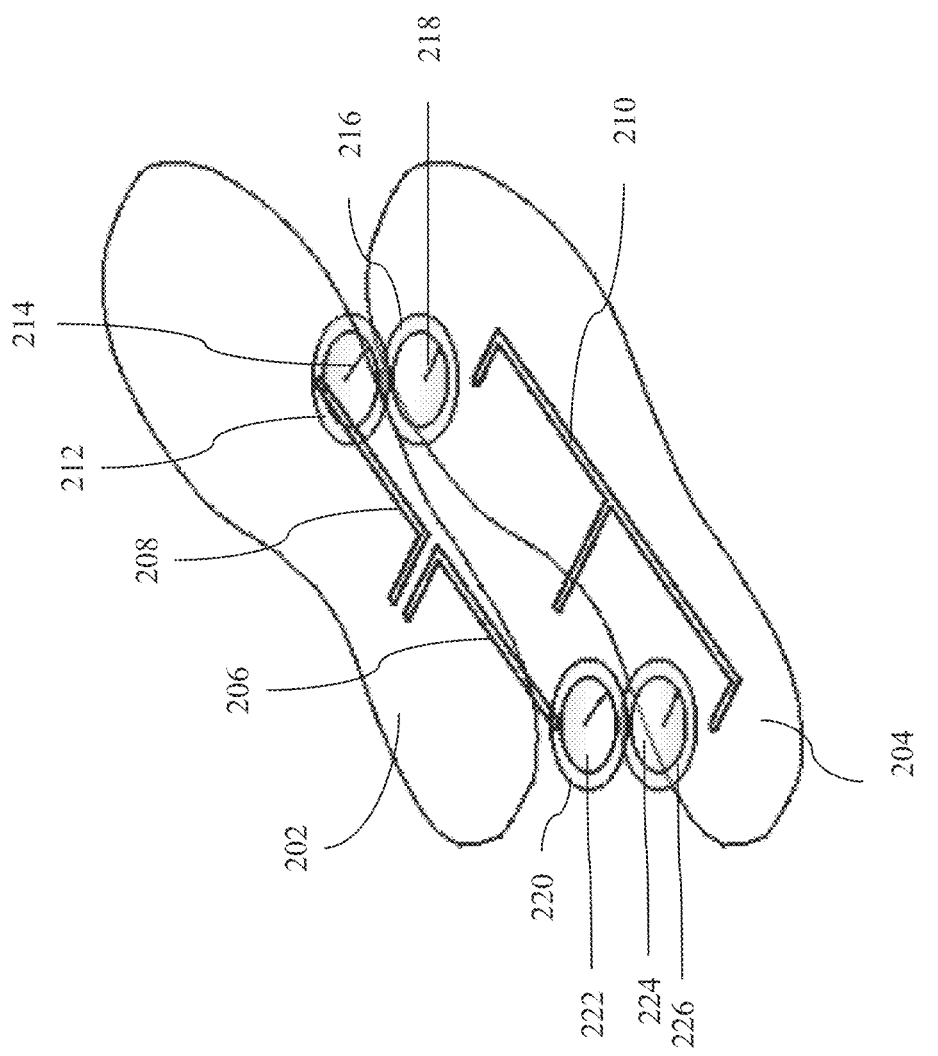
FIGS. 4, 5, and 6 illustrate components of a sensor set, according to an embodiment.
Figure 5:
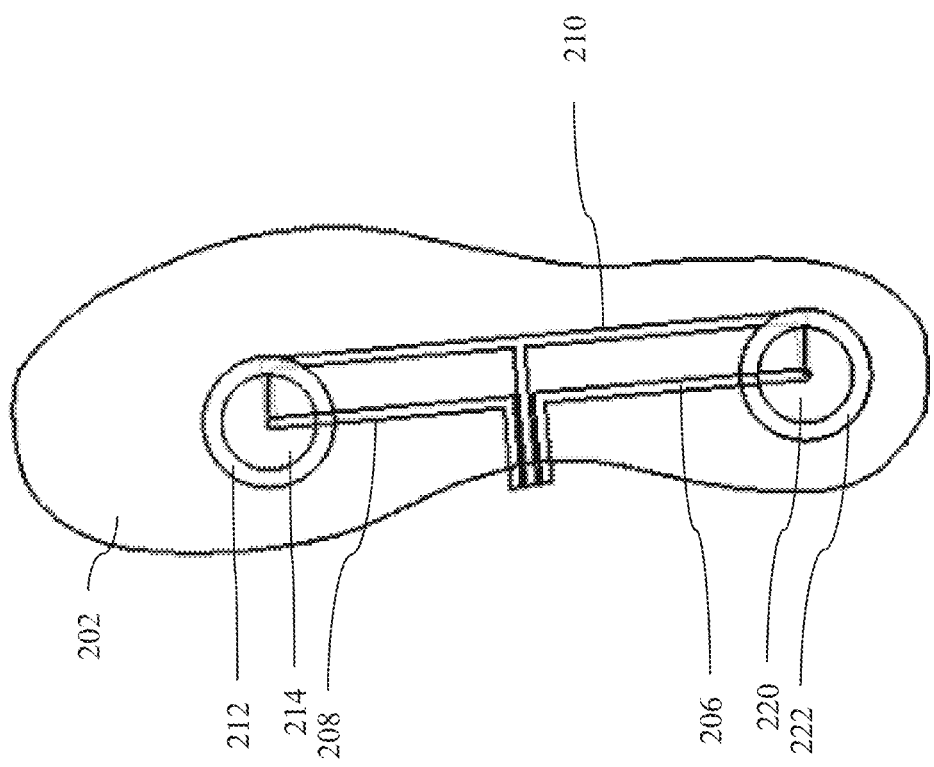
Figure 6:
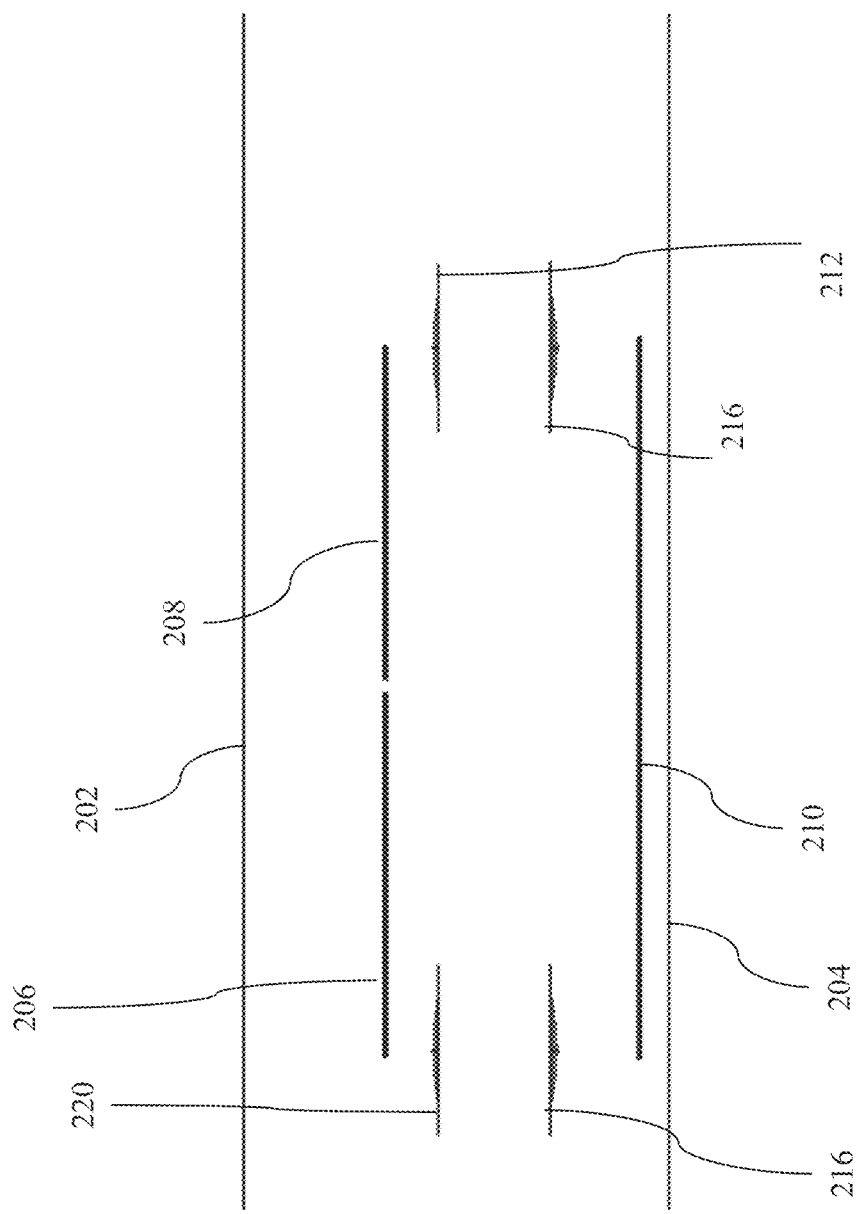

FIGS. 4, 5, and 6 illustrate components of a pressure sensor set, according to an embodiment. FIGS. 4-6 include upper sole 202, lower sole 204, first conductor 206, second conductor 208, third conductor 210, front outer edge 212, front upper air surface 214, lower outer edge 216, front lower air surface 218, rear upper outer edge 220, rear upper air surface 222, rear lower outer edge 226, and rear lower air surface 224.

Each of the first conductor 206, the second conductor 208, and the third conductor 210 may be connected to the module 104 to permit measurement of the resistance of the front and/or rear sensor.

The front upper air surface 214 and the front lower air surface 218 may form the boundary for an air chamber 122 when the front upper outer edge 212 and the front lower outer edge 216 are bonded to form an air-tight seal. Similarly, the rear upper air surface 222 and the rear lower air surface 224 may form an air chamber 122 when the rear upper outer edge 220 and the rear lower outer edge 226 are bonded to form an air tight seal.

The upper sole 202 and the lower sole 204 may be bonded together to form a sole unit that includes both the front and the rear pressure sensor. The upper sole 202 and the lower sole 204 may be made from a variety of materials such as nonconductive fabric or polyester.

C. Mounting of Electronics Module

Figure 7:
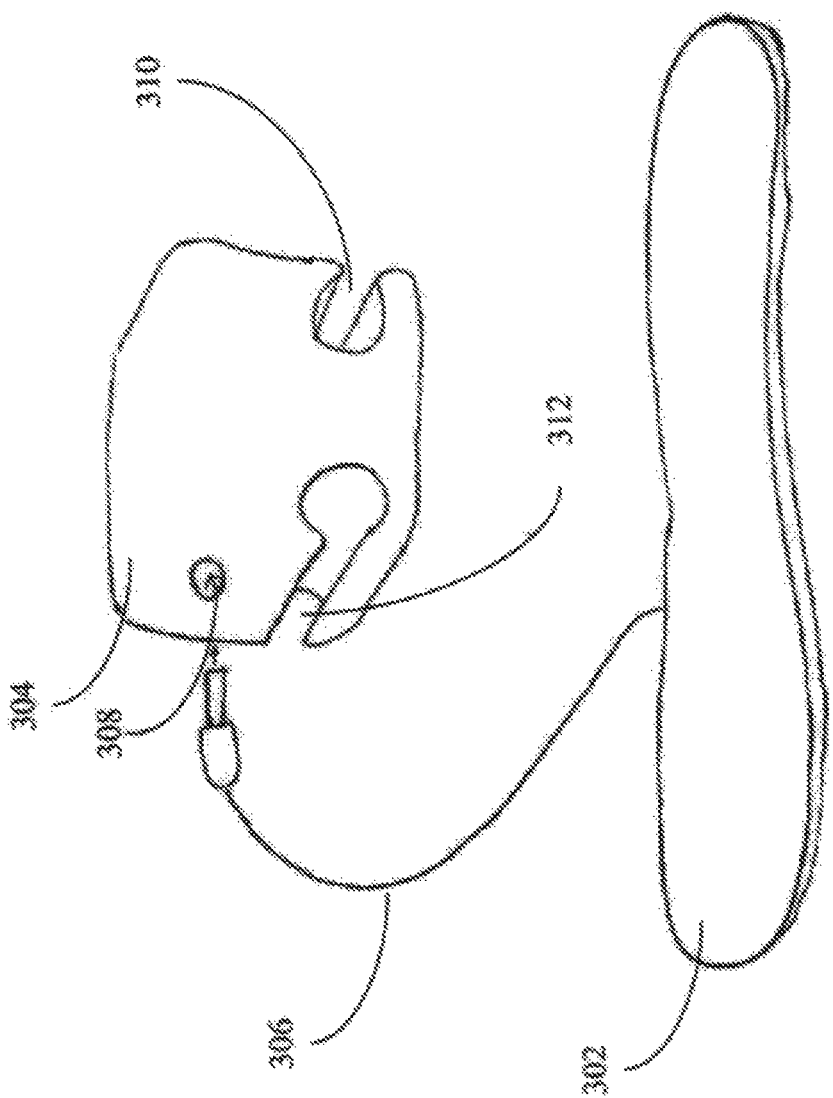
FIGS. 7, 8, and 9 are illustrations of a securing system, according to an embodiment.
Figure 8:
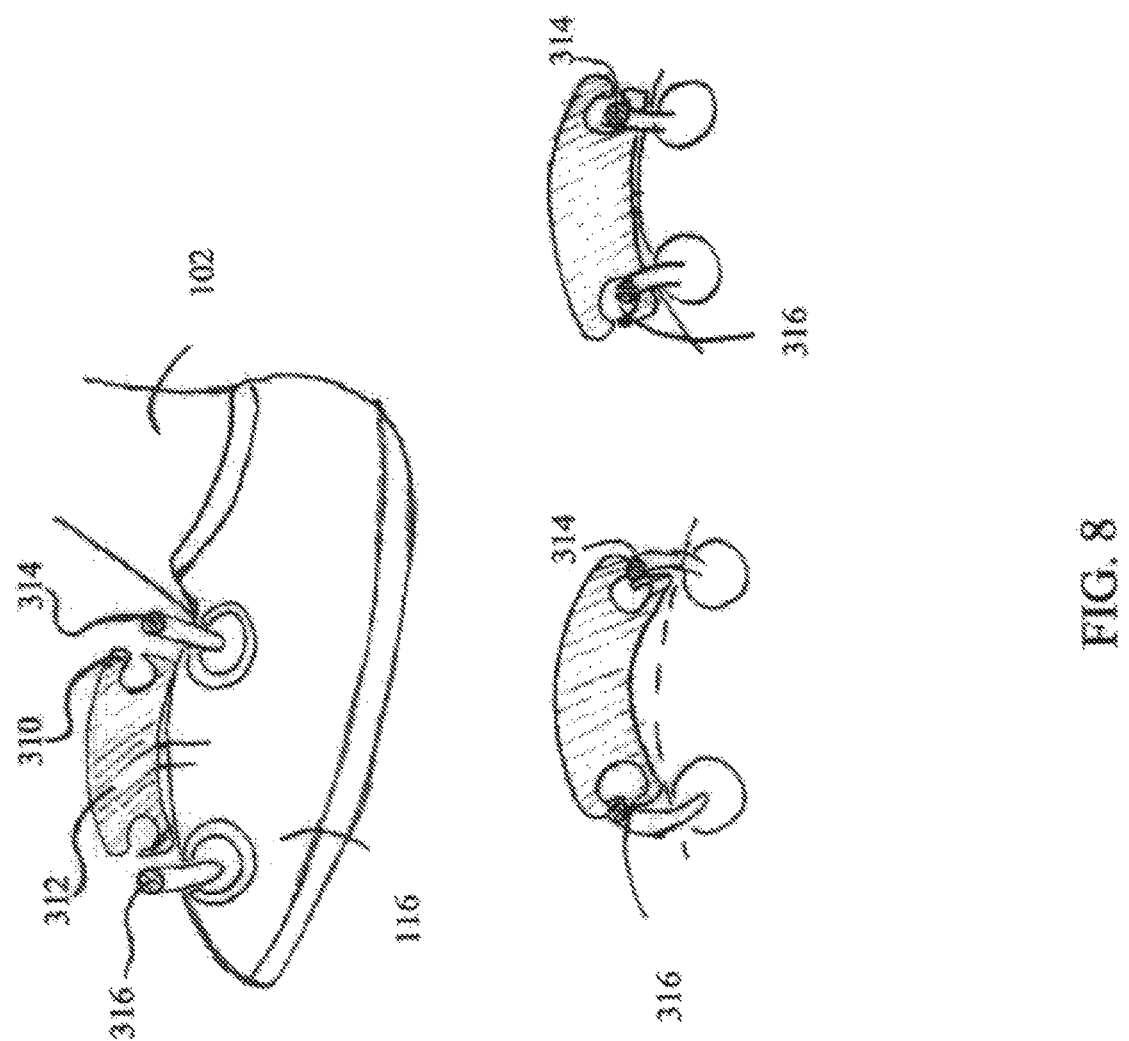
Figure 9:
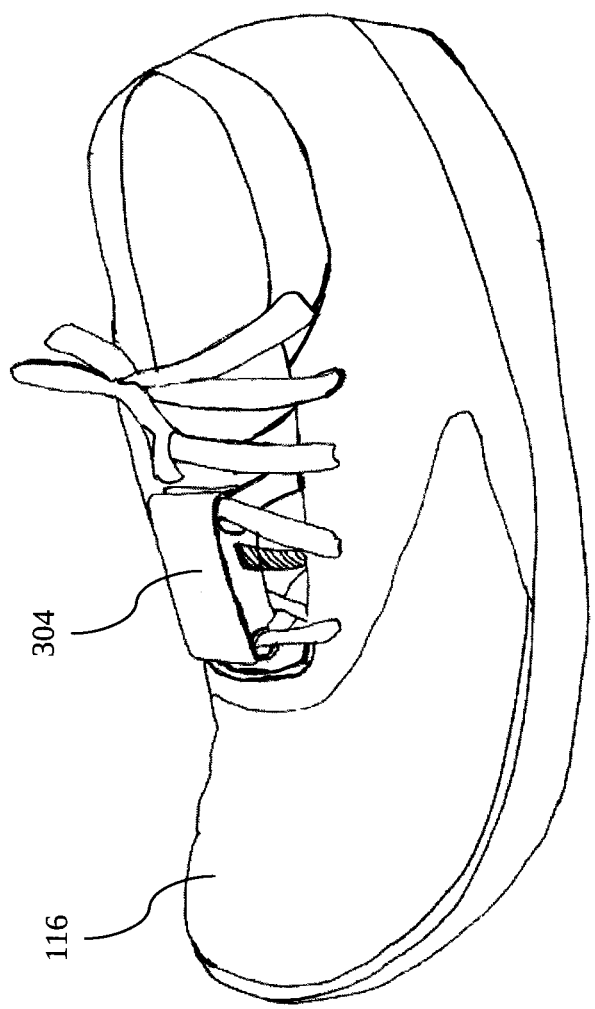

FIGS. 7-9 illustrate how the electronics module 304 may be mounted to a shoe with laces.

FIG. 7 includes a sole 302 that may be formed to include each of the components illustrated in FIGS. 4-6. FIG. 7 also includes an electronics module 304, a cable 306, a port 308, a first slot 312, and a second slot 310.

The first, second, and third conductors may extend from the sole 302 through the cable 306, which may be plugged into a port 308. The electronics module 304 may have a housing formed with the first slot 312 and the second slot 310.

The first slot 312 and the second slot 310 may each extend along a first direction and open laterally outwards from opposite sides (e.g., front and back, or left and right) of the electronics module 304. In this way, the first slot 312 and the second slot 310 may be configured to be clamped to the user's shoes by retaining laterally extending shoelaces within the slots of the electronics module 304.

FIG. 8 includes laces 316 and 314, as well as previously discussed elements such as the user's shoe 116, and slots 312 and 310.

As shown in FIG. 8, the laces of a shoe 116 may be loosened, and moved laterally into the slots 312 and 310, beginning with the top image, and then proceeding to the lower left image, before illustrating full insertion of the laces in the lower right image. The laces may then be tightened to secure the electronics module to the shoe 116.

As shown in FIG. 9, the electronics module 304 may thus be secured to the shoe 116. The electronics module may contain a bluetooth transceiver, one or more accelerometers, batteries, a micro USB interface, and analog to digital convertors for converting pressure signals to electrical signals. The electronics module 304 may include connection port disposed at a rear side or top side to improve retention of a plug. Alternatively, it may be disposed at left or right sides of the electronic module.

It is important that the electronics module 304 be secured to the shoe 116 during a run to measure the runner's pronation, shoe pitch and leg movement up and down. That is to say, it may need to be tightly secured to the shoe to measure the user's shoe movement in X, Y and Z Axis directions. Any wobble of the module while not fully secured to the shoe may cause inaccuracy in the measurement. In some embodiments, the electronics module 304 may be permanently attached to the shoe and/or may be built into the shoe.

The electronics module may be formed using a semi rigid polymer, which may assist with allowing a user to attach and remove the electronics module 304 without removing the laces. In an embodiment, the mouth of the slot 312 and the slot 314 are formed from semi flexible polymer lips. When pressed, the lips may deform, allowing a shoe lace to be inserted. Once pressure has been removed, the lips may spring back to their original shape.

D. Electronics Module

Figure 10:
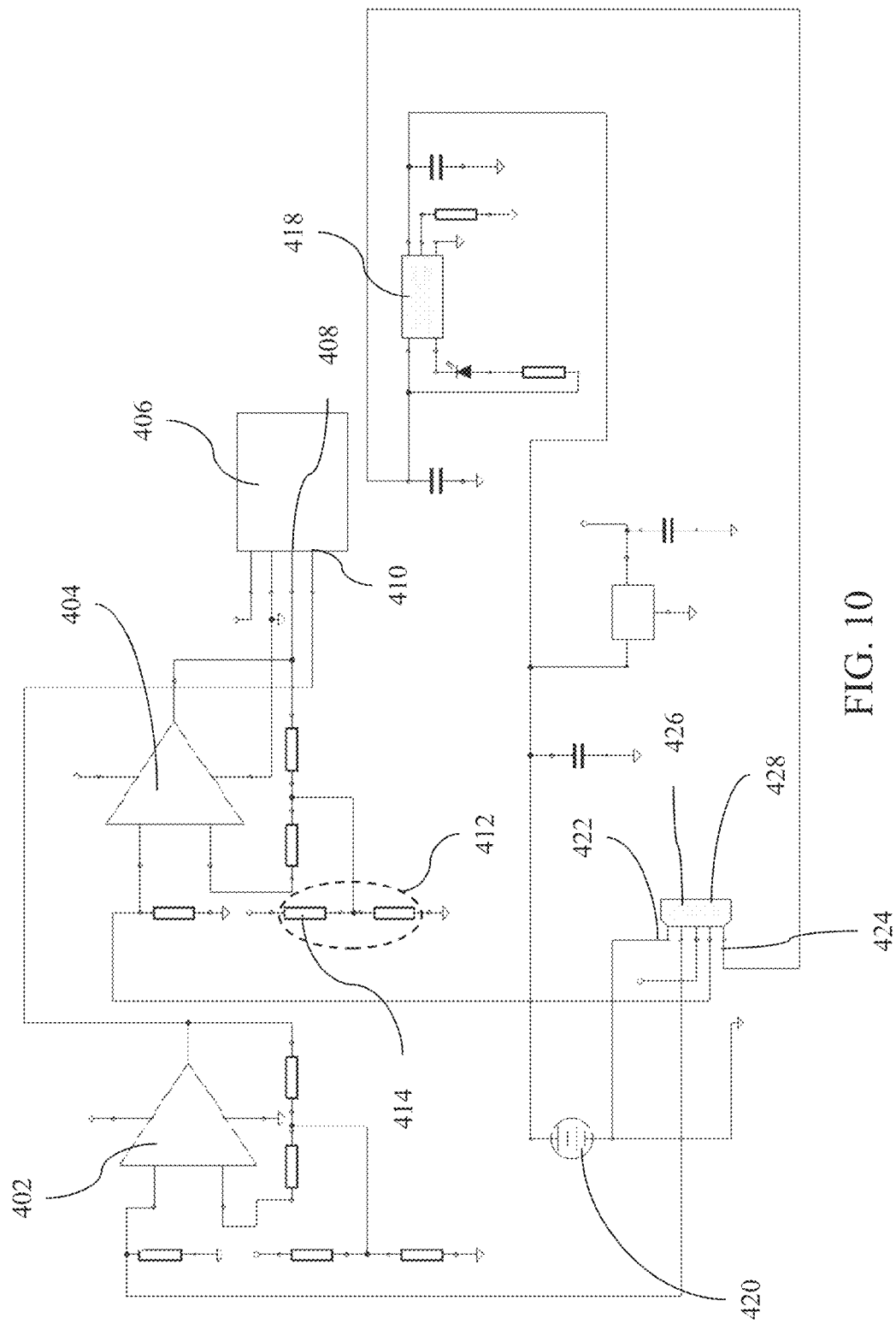
FIG. 10 is a schematic diagram of components of a sensor module, according to an embodiment.

FIG. 10 is a representation of components that may be part of the electronics module. FIG. 10 includes a first op-amp 402, a second op-amp 404, and an A-to-D converter 406 (e.g., analog to digital converter). Also included but not shown are the bluetooth transceiver and the accelerometers. The first op-amp 402 and the second op-amp 404 are used to condition the incoming pressure electrical signal of 0-3 volts to 0-1 volts that is expected by the A-to-D converter.

Channel 408 is connected to front sensor 106 of the insole while channel 410 is connected to the rear sensor 108. The reference voltage of the operation amplifier to compare the incoming 0-3 v signal can be compared to generate an 0-1 v by adjusting the potential divider resistance labelled 414 and 412. By adjusting the resistance ratio of resistor 414 and resistor 412, i.e. resistor 414/(resistor 414+Resistor 412), pressure sensitivity of the feet sensor can be tuned. For example, if the sensor (e.g., front sensor 106, or rear sensor 108) is sensitive, and generates a maximum 1 Volt output from a minimum force from a person standing or walking (e.g., with 50 pounds of force) without running, the reference voltage can be adjusted by adjusting resistor 414 and resistor 412 such that the output of the first and second operational amplifiers are zero when the person is not running. The system may thus automatically zero the sensor output (e.g., from static weight of the user) when the user is standing still.

Additional, the schematic contain a rechargeable lithium-ion polymer battery which is connected to lithium polymer charger 418 which is specially used to charge lithium polymer battery at 100 ma. Lithium-ion polymer charger 418 may shut off if it detects that the battery is fully charged, and will charge the battery when it detects that the battery is below 3V. When fully charged, the battery may be at 4V.

The system may also include a micro USB connector with pins labelled 422, 426, 428 and 424. One connector may be shared by both an external USB cable for battery charging and also a sole connector which is connected to the sensor set while the user is running During a run, the connector will use pins 426, 428 to connect to the sensor set. When the module is used for battery charging, pin 422 is connected to ground and pin 424 is connected to 5V. The 5V can be from a cell phone micro USB port or a normal USB charger.

E. Exemplary User Interfaces

Figure 11:
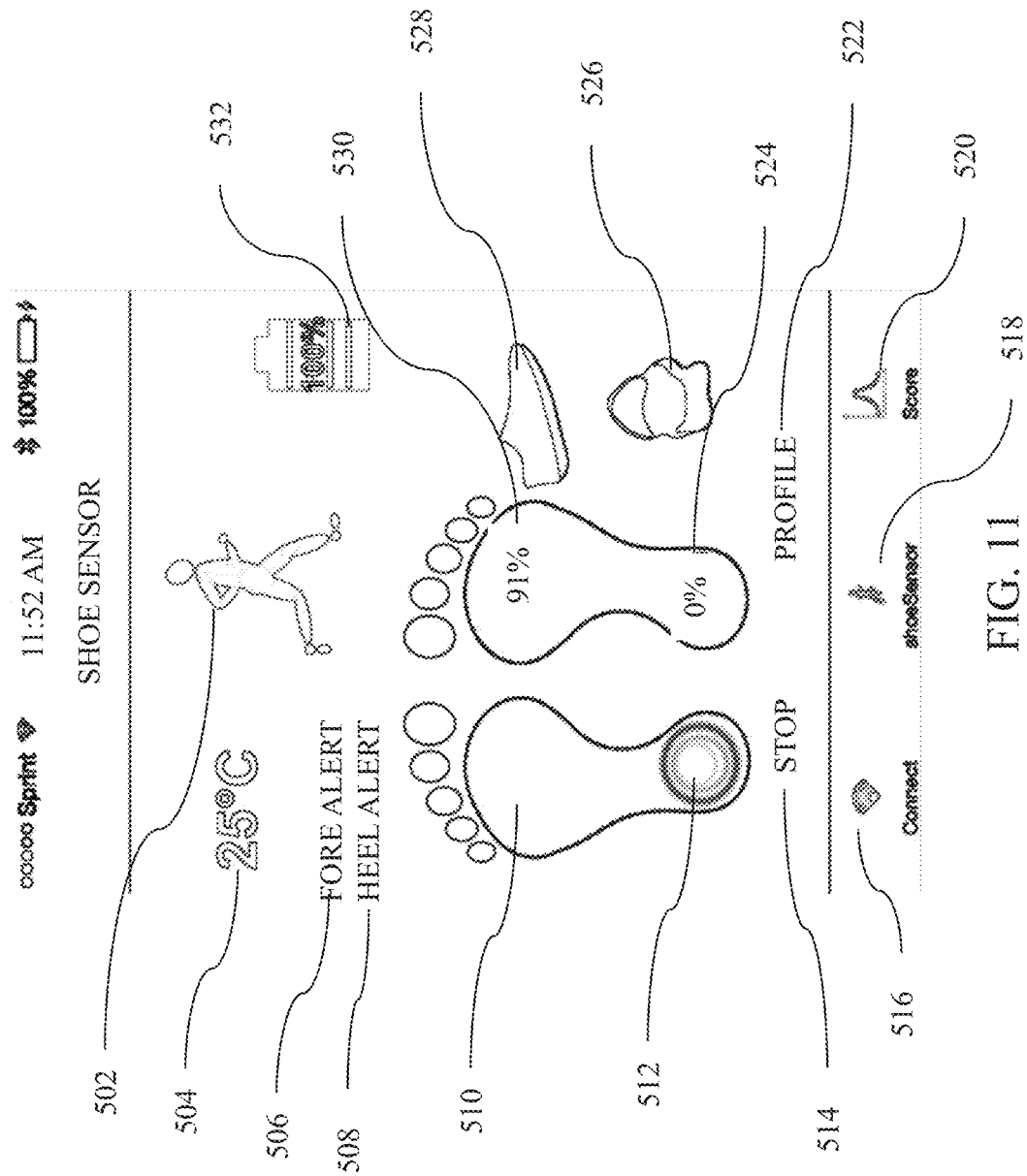
FIGS. 11, 12, 13, and 14 are illustrations of user interfaces, according to an embodiment.
Figure 12:
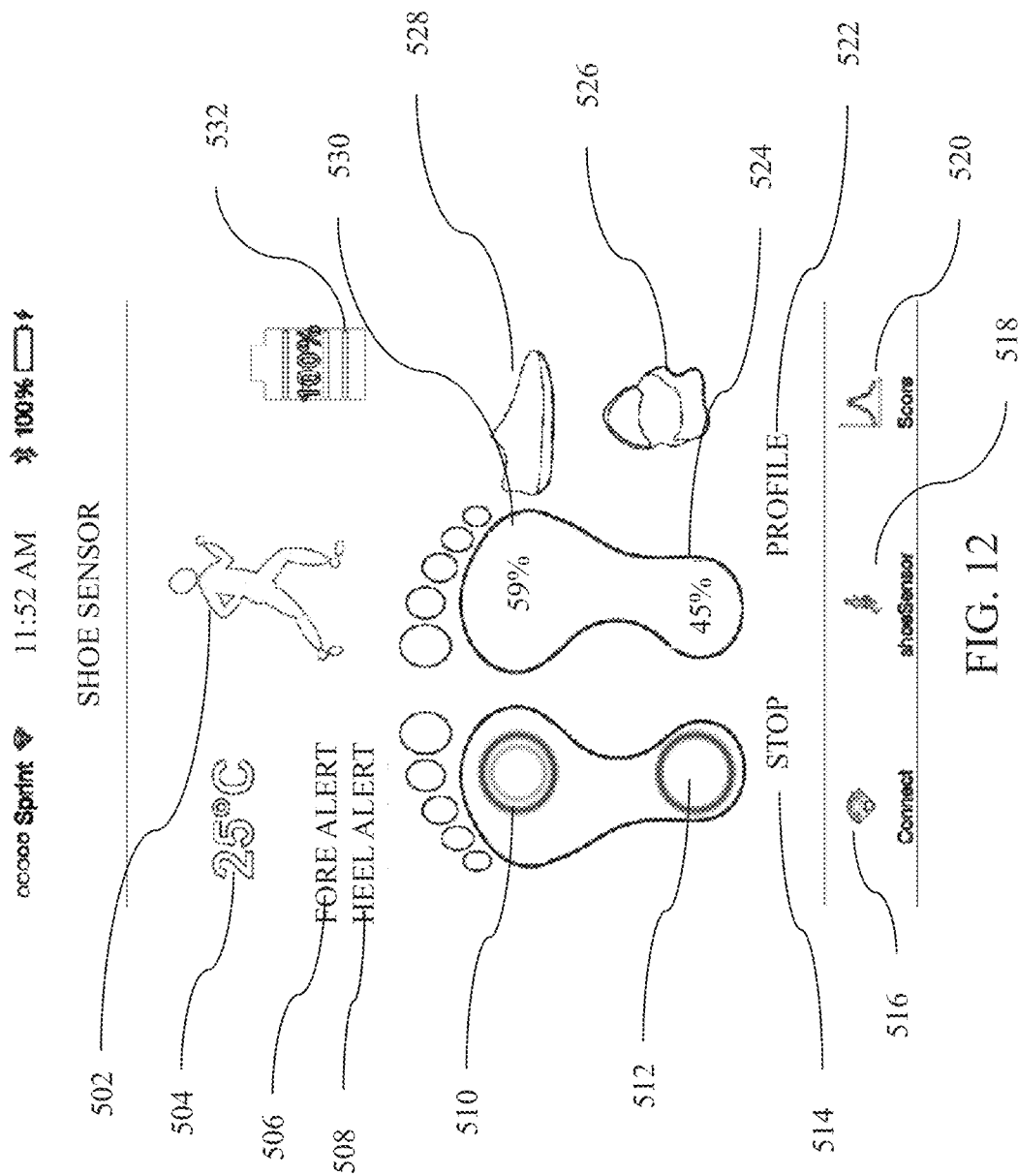
Figure 13:
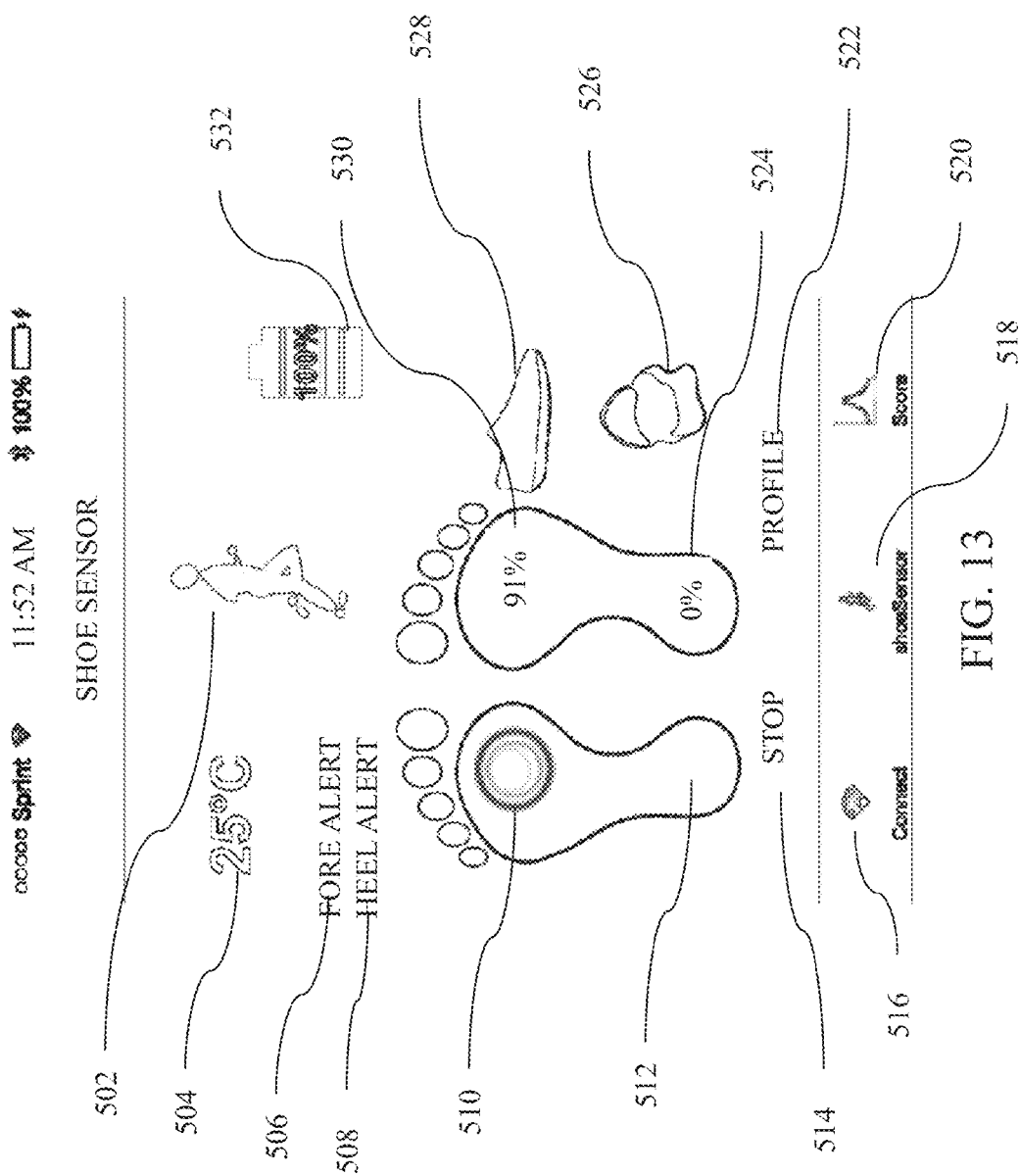

FIGS. 11, 12, 13, and 14 are illustrations of user interfaces, according to an embodiment. FIGS. 11, 12, and 13 include a runner icon 502, a temperature indicator 504, a forefoot alert 506, a heel alert 508, a front pressure indicator 510, a rear pressure indicator 512, a stop button 514, a connect button 516, a shoe sensor button 518, a score button 520, a profile button 522, a heel strike percentage 524, a pronation image 526 (e.g., roll angle), a pitch angle image 528, a front strike percentage 530, and a battery indicator 532.

The runner icon 502 may be a representation of the runner's current running position, based on sensor data. The use of accelerometers (e.g., triaxial linear and/or rotational accelerometers) separately or in combination with pressure sensor data may enable the system to create a real-time representation of the runner. In some embodiments, the pressure sensor data may be used to trigger operation and/or recording of accelerometer data.

The temperature indicator 504 may be used to indicate the present outdoor temperature based on either a temperature sensor or based on weather data provided via an internet connection.

The forefoot alert 506 and the heel alert 508 may be options to respectively turn on an audio alarm when a pressure that exceeds a threshold level is detected at one or both of the front sensor 106 and the rear sensor 108. In some embodiments, the alarm may be a tone, chirp, or other sound that is made audible for a brief period (e.g., half a second) when the threshold is exceeded. In other embodiments, the system may play a sound for running that does not exceed the threshold limits. For example, if the user runs correctly without too much pressure, foot falls may be accompanied by a pleasant sound, and incorrect or excessive pressure footfalls may result in an absence of sound. In other embodiments, the user may listen to music while running, and a discordant note may be played when the alert needs to be sounded.

In other embodiments, other alerts may be provided, such as for over or under pronation, poor body posture, etc. For example, the app may use the pressure sensor data and/or the accelerometer data to determine whether one or more of the user's pronation, body posture, center of gravity, heel strike pressure, and forefoot strike pressure are within a desired range.

In an embodiment, the front pressure indicator 510 and the rear pressure indicator 512 display circles on a foot representation. The more pressure that has been detected, the more circles that may be shown.

The stop button 514 may allow the user to start or stop operation of the system's sensors, which may allow the user to self-monitor their running, with or without generating a profile (e.g., a collected data record).

The connect button 516 may allow a user to connect their smartphone with the electronics module 304, such as via a bluetooth transceiver of the electronics module 304.

The shoe sensor button 518 may allow a user to switch to a current, real-time shoe sensor view, such as interfaces displayed in FIGS. 11, 12, and 13. The score button 520 may allow the user to generate a score based on one or more past runs. The score may be based on their own performance, their prior performance, or based on a competition with others.

The profile button 522 may allow a user to turn on or off the system's profiling of the user's performance.

The heel strike percentage 524 may represent the percentage level that the heel sensor 108 detected relative to a maximum calibrated pressure. Calibration may be performed by allowing the user to jump entirely on the user's heels (e.g., 3, 5, 10 times) before starting to run.

The pronation image 526 (e.g., roll angle) may be a current real-time representation of the user's roll angle of a user's foot. In other embodiments, it may be a static image representing the greatest momentary roll angle of the last step taken.

The pitch angle image 528 may be a current real-time representation of the user's pitch angle of a user's foot. In other embodiments, it may be a static image representing the greatest momentary roll angle of the last step taken.

The front strike percentage 530 may represent the percentage level that the front sensor 106 detected relative to a maximum calibrated pressure. Calibration may be performed by allowing the user to jump entirely on the user's toes multiple times before starting to run.

The battery indicator 532 may represent a remaining battery life of the electronics module 304.

Figure 14:
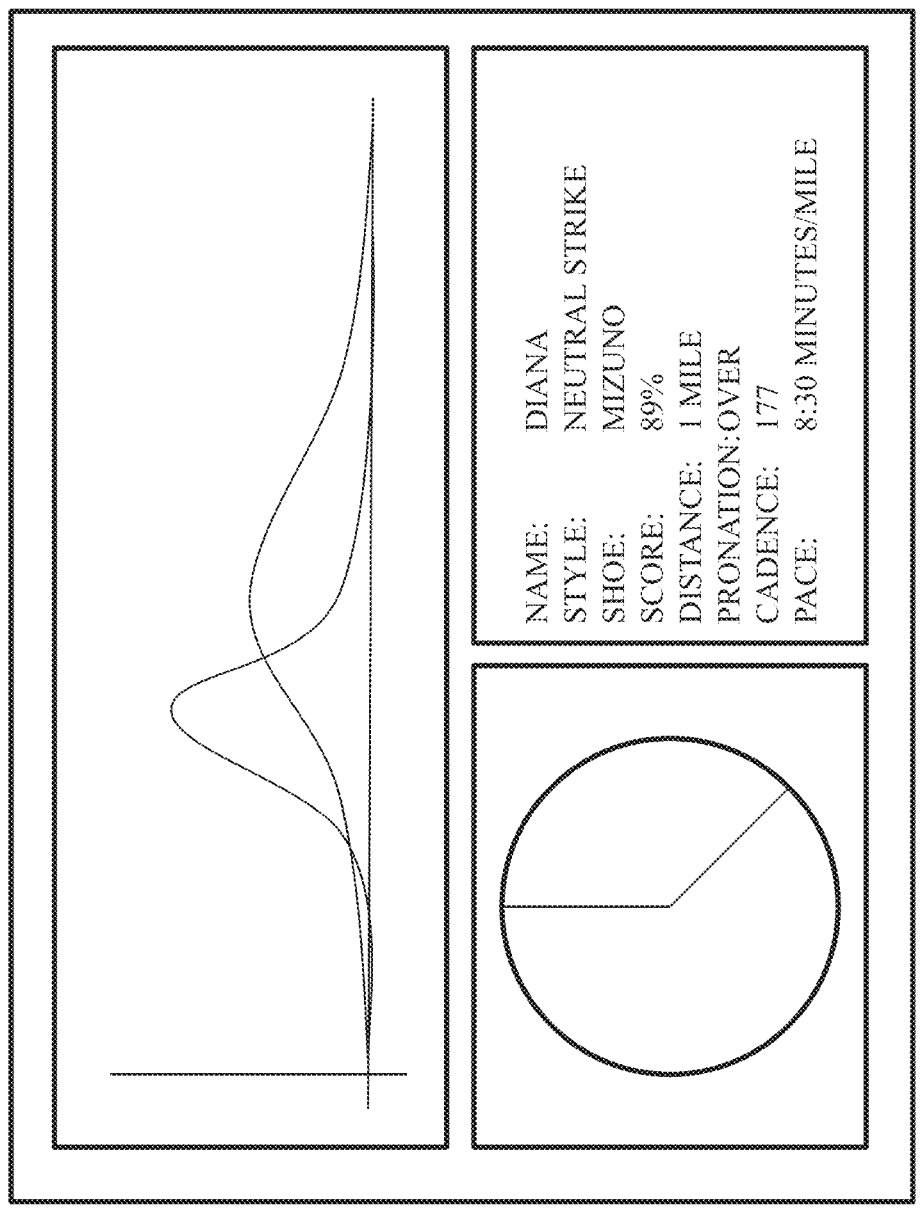

FIG. 14 is an illustration of a user interface according to an embodiment. The view presented may include a pie chart that shoes the average proportion of impacts between the user's front foot and the user's heel.

The interface may further illustrate data collected over the course of a run, including raw sensor data, roll and pitch movement. The data may be categorized by the user name, running style, and shoe type. The system may further present the user's score, the total distance run, any pronation that occurred, the user's cadence, and pace.

Figure 15:
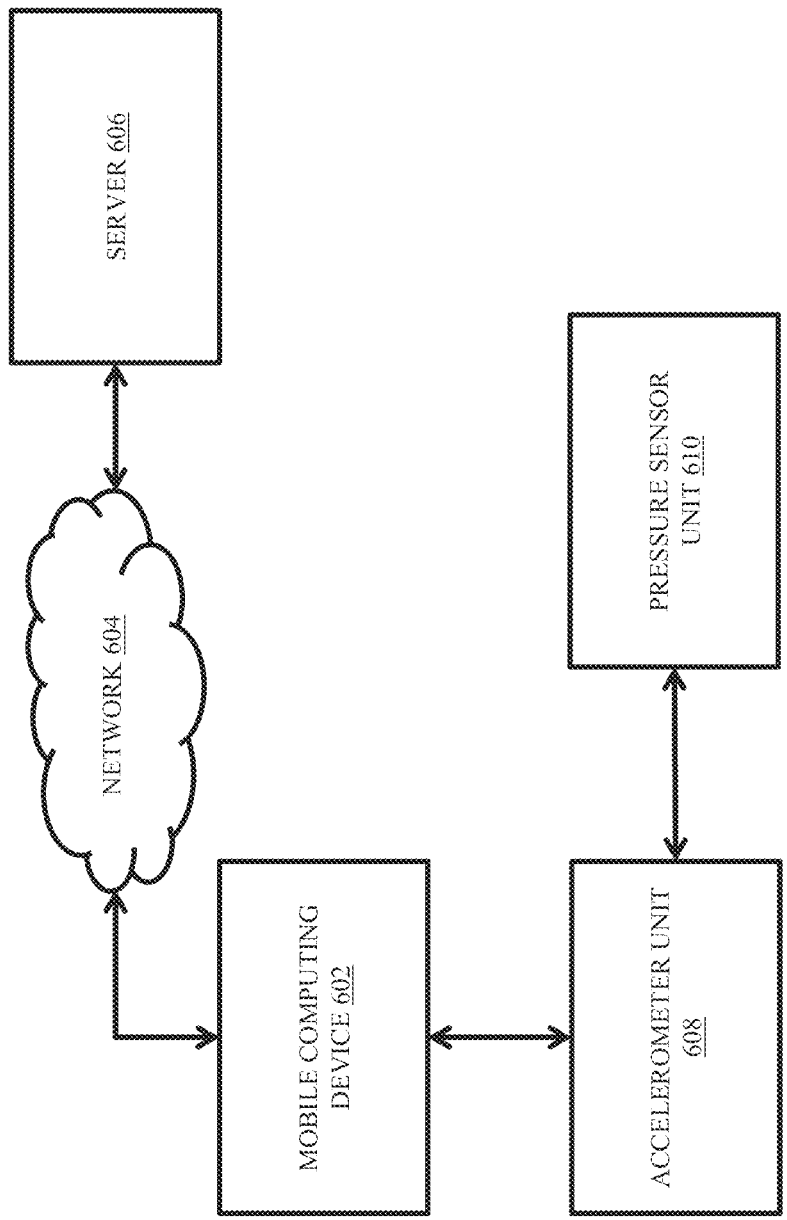
FIG. 15 is an illustration of various components of the system, according to an embodiment.

FIG. 15 is an illustration of various components of the system, according to an embodiment. FIG. 15 includes a mobile computing device 602, a network 604, a server 606, an accelerometer unit 608, and a pressure sensor unit 610. The pressure sensor unit 610 may include the front sensor 106 and the rear sensor 108, and may communicate with the accelerometer unit 608. The pressure sensor data from the pressure sensor unit 610 and the accelerometer data from the accelerometer unit 608 may be sent via Bluetooth to the mobile computing device 602 (e.g., a smartphone running one or more apps).

Figure 16:
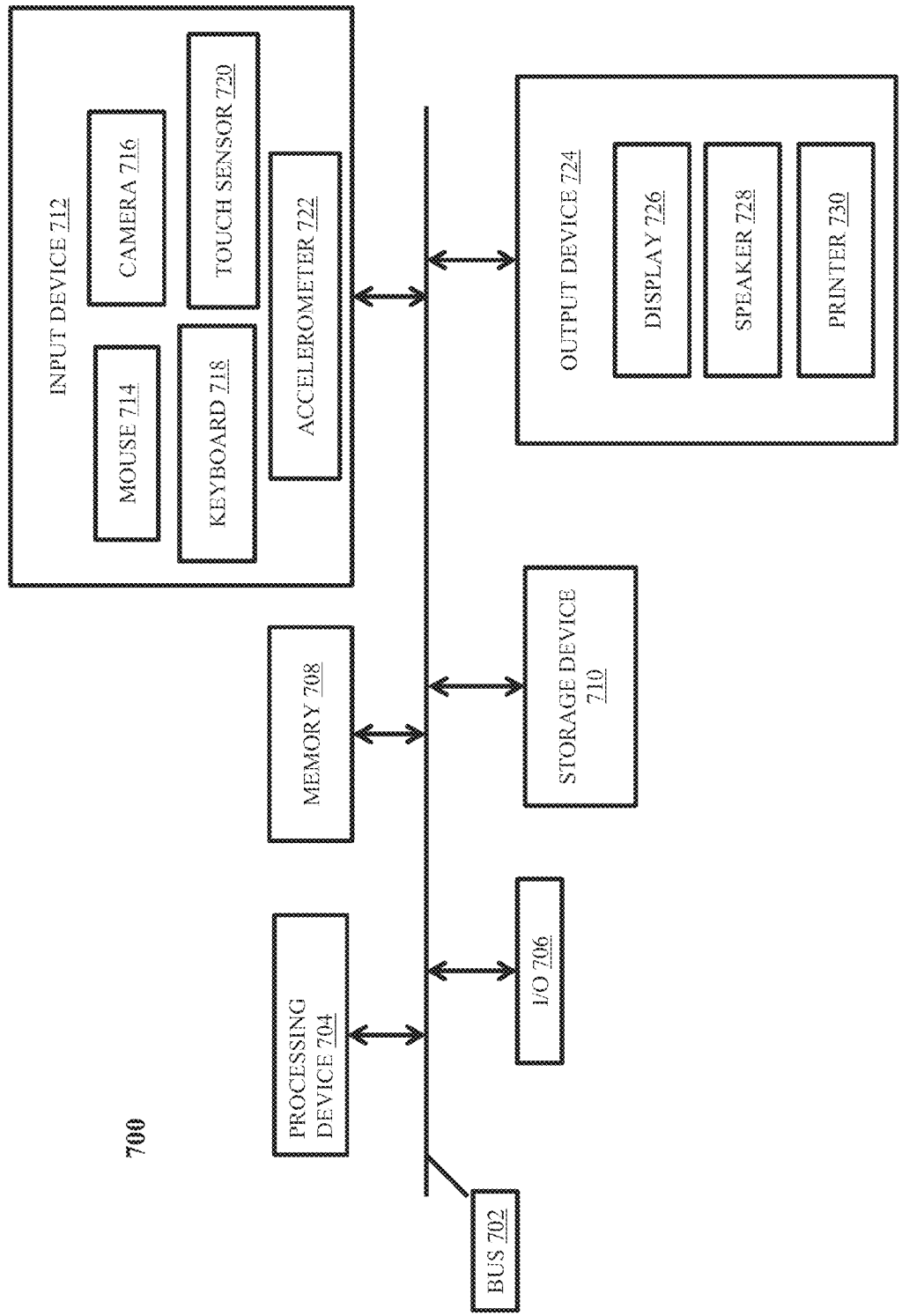
FIG. 16 is an illustration of an exemplary computing system, according to an embodiment.

FIG. 16 is a block diagram of an exemplary computing system that may be used to perform the processes and operations described herein, according to an embodiment. The computing system 700 may represent the mobile computing device (e.g., a smartphone, a tablet, a laptop) that is used to communicate with the shoe-based sensors (e.g., the pressure sensor set, the accelerometers). The computing system 700 may represent the server that communicates with the mobile device.

The computing system 700 may include one or more of each of bus 702, processing device 704, I/O 706, memory 708, storage device 710, input device 712, mouse 714, camera 716, keyboard 718, touch sensor 720, accelerometer 722, output device 724, display 726, speaker 728, and printer 730.

The processing device 704 may include a conventional processor or microprocessor that is configured to interpret and execute a set of instructions. The processing device 704 may communicate with each of the other components in the computing device 700 via the bus 704, such to obtain instructions stored in the memory 708 and/or the storage device 710. The processing device 704 may further be configured to receive inputs from the input device 702, and to provide outputs via the output device 724. The bus 704 may permit communication between the components of the computing device 700.

The memory 708 may include RAM and/or ROM. The storage device 710 may include magnetic hard drives, flash media, magnetic media, optical media, or another type of physical device that stores information for the processing device 704. The storage device 710 may include tangible machine-readable media and/or the corresponding drive for reading and/or writing to the machine-readable media. The memory 708 and/or the storage device 710 may store a set of instructions detailing a method that when executed by one or more processing devices cause the one or more processing devices to perform the method.

The input device 712 may be used by a user to provide information to the processing device 704. The input device 712 may include one or more of the mouse 714, camera 716, keyboard 718, touch sensor 720, and/or accelerometer 722. The output device 724 may be used by the processing device 704 to provide audio and/or visual output to one or more users. The output device 724 may include the display 726, speaker 728, and printer 730.

The I/O 706 may be any device that permits the processing device 704 to communicate with other devices and/or networks. For example, the I/O 706 may include a modem, a network card, or other interface. The I/O 706 may permit communication with wired, wireless, and/or optical systems (e.g., Bluetooth, USB, etc.). The I/O 706 may further permit peripheral devices to be connected to the computing device 700, or to pair the computing device 700 with other computing devices.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiments, methods, and examples, but by all embodiments and methods within the scope and spirit of the invention.

Although only some embodiments of the present invention have been described in detail above, those skilled in the art will readily appreciate that many modifications are possible in the embodiments without materially departing from the novel teachings and advantages of this invention. Accordingly, all such modifications are intended to be included within scope of this invention.

What is claimed is:

1. A system for processing runner data, the system comprising:
   a pressure sensor set having a first pressure sensor disposed in a footbed, the first pressure sensor comprising a first conductive polyolefin sheet and a first gas chamber formed at least in part by the first conductive polyolefin sheet, wherein the first gas chamber is airtight sealed;
   an electronics module coupled to the pressure sensor set, the electronics module including a first accelerometer, and a second accelerometer.

2. The system of claim 1, wherein the first pressure sensor includes a second conductive polyolefin sheet, the first gas chamber being formed in part by the first conductive polyolefin sheet and the second conductive polyolefin sheet.

3. The system of claim 2, wherein the first conductive polyolefin sheet and the second conductive polyolefin sheet are bonded together at a perimeter that encircles the first gas chamber.

4. The system of claim 1, wherein the first gas chamber enlarges a pressure sensing range of the first pressure sensor.

5. The system of claim 1, wherein the electronics module is coupled to the first pressure sensor via a first conductor and a ground conductor.

6. The system of claim 1, wherein the pressure sensor set includes a second pressure sensor comprising a third conductive polyolefin sheet and a second gas chamber formed at least in part by the third conductive polyolefin sheet, wherein the second gas chamber is air-tight sealed.

7. The system of claim 6, wherein the electronics module is coupled to the first pressure sensor using a first conductor and a third conductor, and wherein the electronics module is coupled to the second pressure sensor using a second conductor and the third conductor.

8. The system of claim 1, wherein the electronics module includes a third accelerometer.

9. The system of claim 1, wherein the electronics module includes a housing formed with two slots that are oppositely disposed on the housing, each slot being configured to receive at least one shoelace that secures the electronics module to a shoe.

10. The system of claim 9, wherein each slot includes a flexible flange that extends across the slot opening, the flange being configured to bend when a shoelace is pressed into the slot, and to spring back into place after the shoelace has been pressed far enough into the slot to pass the flange.

11. The system of claim 1, wherein the footbed is a removable shoe sole.

12. The system of claim 1, wherein the footbed is bonded to a shoe.

13. The system of claim 1, wherein system automatically recalibrates its sensitivity when the accelerometers detect that a user is not moving and that the output of the pressure sensor has held a maximum output level for more than a threshold period of time.

14. The system of claim 1, wherein the system is configured to wirelessly relay accelerometer data and pressure sensor data to a smartphone for developing a runner profile.

15. The system of claim 14, wherein the runner profile indicates whether at least one of the user's feet rotates improperly around a roll axis.

16. A system for processing runner data, the system comprising:
a pressure sensor set having a first pressure sensor and a second pressure sensor each disposed in a removable shoe insert, each of the first pressure sensor and the second pressure sensor comprising a first conductive polyolefin sheet, a second conductive polyolefin sheet, and a gas chamber formed at least in part by the first conductive polyolefin sheet and the second conductive polyolefin sheet, wherein the gas chamber is air-tight sealed;
an electronics module coupled to the pressure sensor set, the electronics module including a first accelerometer, a second accelerometer, and a third accelerometer, the electronics module having a housing configured to be secured to the top of a user's running shoe.

17. The system of claim 16, wherein the first conductive polyolefin sheet and the second conductive polyolefin sheet are bonded together at a perimeter that encircles each enclosed gas chamber.

18. The system of claim 16, wherein each gas chamber enlarges a pressure sensing range of the first pressure sensor and the second pressure sensor.

19. The system of claim 16, wherein the electronics module is coupled to the first pressure sensor via a first conductor and a ground conductor, and wherein the electronics module is coupled to the second pressure sensor via the second conductor and the ground conductor.

* * * * *